United States Patent [19]

Friedman et al.

[11] Patent Number: 4,802,484
[45] Date of Patent: * Feb. 7, 1989

[54] METHOD AND APPARATUS TO MONITOR ASYMMETRIC AND INTERHEMISPHERIC BRAIN FUNCTIONS

[75] Inventors: Ernest H. Friedman, 1831 Forest Hills Blvd., East Cleveland, Ohio 44112; Gary G. Sanders, Lakewood, Ohio; Steven L. Hunter, Livermore, Calif.

[73] Assignee: Ernest H. Friedman, Cleveland, Ohio

[*] Notice: The portion of the term of this patent subsequent to Oct. 1, 2002 has been disclaimed.

[21] Appl. No.: 77,550

[22] PCT Filed: Sep. 27, 1985

[86] PCT No.: PCT/US85/01909
§ 371 Date: May 22, 1987
§ 102(e) Date: May 22, 1987

[87] PCT Pub. No.: WO87/01922
PCT Pub. Date: Apr. 9, 1987

Related U.S. Application Data

[63] Continuation-in-part of Ser. No. 503,821, Jun. 13, 1983, Pat. No. 4,543,957.

[51] Int. Cl.$^4$ ............................................. A61B 5/00
[52] U.S. Cl. ................................... 128/630; 128/773; 364/413.01; 364/413.05
[58] Field of Search ............... 128/630, 773, 731–732, 128/905; 364/409, 413, 419; 434/28–29, 33, 167, 169

[56] References Cited

U.S. PATENT DOCUMENTS 3,983,535  9/1976  Herbst et al.
4,543,957  10/1985  Friedman et al. ................. 128/630

OTHER PUBLICATIONS

Michael S. Gassaniga, "The Bisected Brain", N.Y. Academic Press, 1970, pp. (title pages), 90, 91, 140, 142–143, 162–172.
Peter Wolff, M.D., "Brain Hemispheres Function as Unit in Complex Tasks", Psychiatric News, Aug. 6, 1982.
Science, vol. 228, pp. 1217–1219, Jun. 7, 1985.
David Eidelberg, M.D. and Albert M. Galaburda, M.D., "Inferior Parietal Lobule", Arch Neurol-Vol. 41, Aug. 1984, pp. 843–852.
Science, vol. 229, Jul. 1985, pp. 62–65.

Primary Examiner—Francis J. Jaworski
Attorney, Agent, or Firm—Pearne, Gordon, McCoy & Granger

[57] ABSTRACT

Responses of a human subject may be by voice, hand or foot movement, or bodily secretions, as examples. A hiatus of such responses may be termed a lapse in the continuity of the response, including a hesitation pause in the voice, hesitation in the movement of writing, a movement of hand or foot on a monitored control of a motor vehicle or vehicle simulator, or pulsatile bodily secretions on a monitored control of an implantable insulin pump. In a voice response, the hesitation pause may be more than about one second in the voice of a subject during a dialogue or monologue. The hiatus rate of such responses is indicated by the present apparatus, as in the average hiatus duration for two or more hiatus rates. The dominant hiatus rate is also determined and indicated. A microprocessor is utilized in such determination.

13 Claims, 8 Drawing Sheets

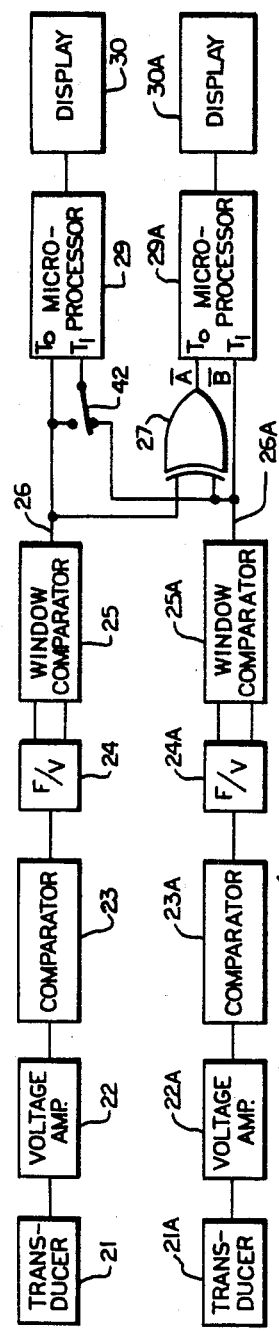
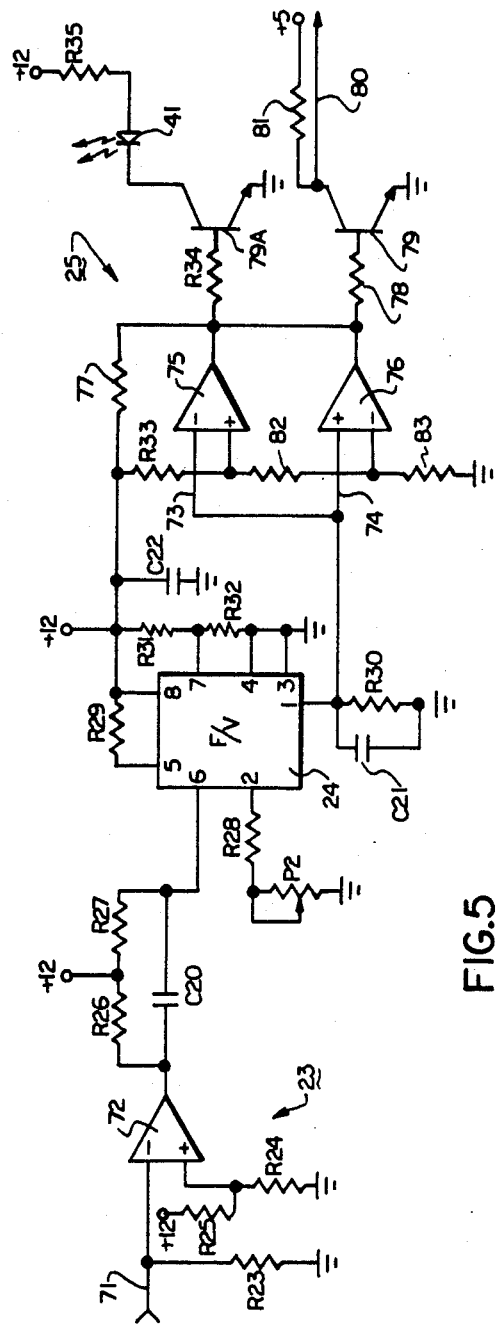
FIG. 1
FIG. 5

METHOD AND APPARATUS TO MONITOR ASYMMETRIC AND INTERHEMISPHERIC BRAIN FUNCTIONS

This application is a continuation-in-part of our patent application entitled "Human Response Apparatus and Method," U.S. Ser. No. 503,821, filed June 13, 1983 (now U.S. Pat. No. 4,543,957, issued Oct. 1, 1985), the disclosure of which is incorporated herein by reference.

BACKGROUND OF THE INVENTION

The parent application discloses method and apparatus to monitor behavioral correlates of brain function. The rate of speech pausing or hiatus rates of other neuromotor functions correlates negatively to the efficiency of dominant, usually left brain hemisphere function, such as in Broca's Aphasia and Parkinson's Disease; longer, less recurrent pauses or hiatuses are indicators of efficiency of the right brain hemisphere, i.e., echo-time (MS Gazzaniga, *The Bisected Brain*, New York Academic Press, 1970).

Coordinated hemispheric functioning to perform complex tasks, as described by P. Wolff on Aug. 6, 1982, cited in the parent patent, is mediated by interhemispheric transmission time in the order of 2.5 to 20 msec. Longer times are required to process visual stimuli by the occipital cortex compared with the processing of non-visual stimuli by other regions of the cerebral cortex. A complex activity such as focal visual attention for red-green discrimination, which necessarily is mediated by the opponent cells in the visual cortex, requires 16.6 msec processing time (*Science* 228: 1217–1219, 1985).

An increase in hiatus time from lower to higher fluency, utilizing software disclosed in the parent patent expanded to the fourth decimal place, is a measure of a shift from left to right hemispheric brain activity, hence, an objective indicator of interhemispheric transmission time.

U.S. Pat. No. 3,983,535 discloses that muscle contractions during highly practiced motions such as signature writing are controlled without sensory feedback to an accuracy of about 5 msec. Hand-brain-hand propagation time restricts feedback effects to be greater than 100 msec. Such longer time intervals typically occur during a pause in writing between the first and last name. U.S. Pat. No. 3,983,535 makes no provision for monitoring these pauses to identify writing style that is consistent over time and that can enhance accuracy in signature verification. Similarly, this method and apparatus may be utilized in testing and training pilot trainees on a flight simulator where neuromotor responses are likewise monitored in reaction to sensory inputs to the two hemispheres. The right eye only sees liquid crystal digital displays of helicopter functions which are processed by the mathematically oriented left hemisphere while the left eye perceives real word scenes on the simulator which are processed primarily by the spatially talented right hemisphere.

These neuromotor activities are subserved by neural motor networks in the left hemisphere and specific areas in the right hemisphere that maintain vigilance (Arch Neurol 41: 843–852, 1984). Motoric activity is subserved by dopamine (*Science* 229: 62–65, 1985).

By using the greater than 100 msec threshold, this invention discloses newer data and methods and apparatus for monitoring motor cortex activity on the left rather than just speech at the one second plus threshold for Broca's Area as disclosed in the prior patents and application.

SUMMARY OF THE INVENTION

The present invention relates to a method and apparatus for monitoring asymmetric and interhemispheric brain function, such as speech, keystrokes on a computer terminal, manual movements of a pen, or steering wheel and pedal actuation in a motor vehicle or vehicle simulator, for example. It also relates to a human response such as bodily secretions. Apparatus and a method are disclosed for determining and displaying hiatus frequency and duration. A hiatus is a lapse in the continuity of the human or neuromotor response. If a response is a voice response, a hiatus is defined as a timed interruption in the response, the average rate of hesitation pauses being measured in a given time segment, and these hesitation pause rates are sorted into at least two levels or frequency bands, and finally, there is an indicator to indicate to human sensors for transmission to the brain the dominant hiatus or hesitation pause level and the average hiatus or pause duration for each level. This determination and display may be used by the health caretaker, trainer, or teacher, or the individual himself, in several ways. It may be used to assess and coordinate the left and right cerebral hemisphere interactions; it may be used to diagnose endogenous depression; it may be used to modify coronary-prone behavior; and it may be used as an aid in approximating the pace of the conversational partner. The apparatus utilizes microprocessor technology to determine pause frequency and pause duration, and has a dual display of the pause durations and frequency of each of two persons having a dialogue.

A feature of the present invention is that a multiple display is provided. This permits neuromotor response comparison, namely neuromotor efficiency at two or more levels, by comparing responses of two or more interacting individuals or two or more similar responses by one individual. The neuromotor response may include vocal fluency and an end result can be the potential use in organizational development to teach communication skills in staff training. This can be a comparison of one person with one another, and hence would be interpersonal interaction.

Another potential use is in evaluating handedness in terms of finger dexterity, e.g., right hand versus left hand, and utilizing keyboards similar to typewriter keyboards, wherein the right-handed dexterity is compared with the left-handed dexterity. This is intrapersonal evaluation. The utility is to diagnose handedness to discover imbalance that may be corrected with training.

Other intrapersonal comparisons are neuromotor responses between the hands, e.g., steering wheel and the right and left feet of a person, e.g., the accelerator, brake, and clutch controls on a motorized vehicle. This has utility for driver training in a simulator; and on-line monitoring in a motor vehicle by transmission via radio frequency to a control monitor, and retrospective evaluation, as in a "flight recorder." It has usefulness in developing the driver's contribution to fuel efficiency by minimizing pumping the accelerator and limiting the use of the brake. It also may be used to measure driver efficiency in terms of mental depression and coronary-prone behavior, e.g., suicide and susceptibility to heart attack at the wheel of the vehicle. If the multiple display is utilized as a method of driver training, it may be presented after the trip is completed upon turning off the ignition so as not to distract the driver enroute.

The apparatus and method permit the evaluation of four different factors:

(1) the dominant or average frequency level of the hiatuses or hesitation pauses, which may be indicated by a voice synthesizer or illumination of red, yellow, or green indicator lights, a green light indicating high efficiency as the desired response.

(2) the peak efficiency level, which is shown by an indicator such as a digital readout juxtaposed to these lights.

(3) a measure of the flexibility of the speech pattern of the subject so that a determination can be made as to how the hesitation pattern may be changed by modifying the pause durations in each of the three frequency ranges. As in all servocontrol mechanisms, the output is constant, namely, frequency times duration is a constant. The therapeutic benefit is by having patients see how increasing pause duration allows adequate time to collect thoughts, thus leading to a decreased rate of speech hesitation. Decreasing pause frequency by increasing pause duration results in melodic speech or prosody, a right brain function.

(4) a dual display for indication of how the subject corresponds in speech fluency and prosody with another person.

An analysis of over 500 dialogues indicates that hesitation pause durations have a mean of about 1.50 seconds with a standard deviation of 0.33 second. Accordingly, the present apparatus and method permit a means of identifying hestitation pause durations at high, middle, and low coronary risk (U.S. Pat. No. 4,278,096) and matching of dominant pause durations in a dual display format to determine interpersonal harmony of pace at the 95 percent level of confidence. This 95 percent level of confidence may be defined as the probability P being less than 0.05 discordance, namely, there being only one chance in 20 that a person is classified in one group when he should actually have been classified in the other group.

When speaking with a dysfluent person, the instrument user especially strives to attain a match by achieving higher fluency, e.g., green versus yellow or red light, or yellow versus red light. This provides a balance or a model for the dysfluent conversational partner. An even closer approximation or similar directional change of pause durations at higher fluency levels immediately adjacent to the dominant modes is indicative of adaptive interpersonal interaction.

The problem to be solved, therefore, is how to construct apparatus and how to utilize a method of determining pause frequency and pause duration of a human neuromotor response.

The problem is solved by a human response system for determining the rate of hiatuses between neuromotor responses of a human subject, comprising in combination, transducer means responsive to at least one type of monitored neuromotor response of the subject who is subjected to sensory inputs to the right and left hemispheres of the brain, hiatus means connected to said transducer means to determine successive occurrence of a hiatus between predetermined neuromotor responses of said type of the subject, with each hiatus defined as the absence of said at least one type of monitored neuromotor responses for a predetermined time interval bounded by the predetermined neuromotor responses, rate means connected to said hiatus means to determine the average hiatus rate in a given segment of the predetermined neuromotor response of the subject, sorting means to sort the average hiatus rate into one of at least two levels of response, and means to indicate the average time duration of the individual hiatuses for each of the at least two rate levels.

The problem is also solved by the method of determining hiatus frequency and duration of a human neuromotor response, comprising in combination, determining the occurrence of each of a plurality of hiatuses in the neuromotor response of a human subject, each hiatus defined as a lapse in the continuity of the response, measuring the average hiatus rate in a given time segment of a response, sorting the hiatuses into at least two rate levels, and indicating to human sensors for conscious awareness the hiatus rate level which was dominant relative to the others of the at least two rate levels and the average hiatus duration of such level.

Accordingly, an object of the invention is to provide apparatus and method for determining, storing and displaying hiatus frequency and hiatus duration of a human neuromotor response.

Other objects and a fuller understanding of the invention may be had by referring to the following description and claims, taken in conjunction with the accompanying drawing.

BRIEF DESCRIPTION OF THE DRAWINGS

FIG. 1 is a block diagram of a human neuromotor response circuit in accordance with the invention;

FIG. 5 is a schematic diagram of the preferred form of comparator, frequency-to-voltage converter, and window comparator of FIG. 1;

DETAILED DESCRIPTION OF THE PREFERRED EMBODIMENTS

Figure 2:
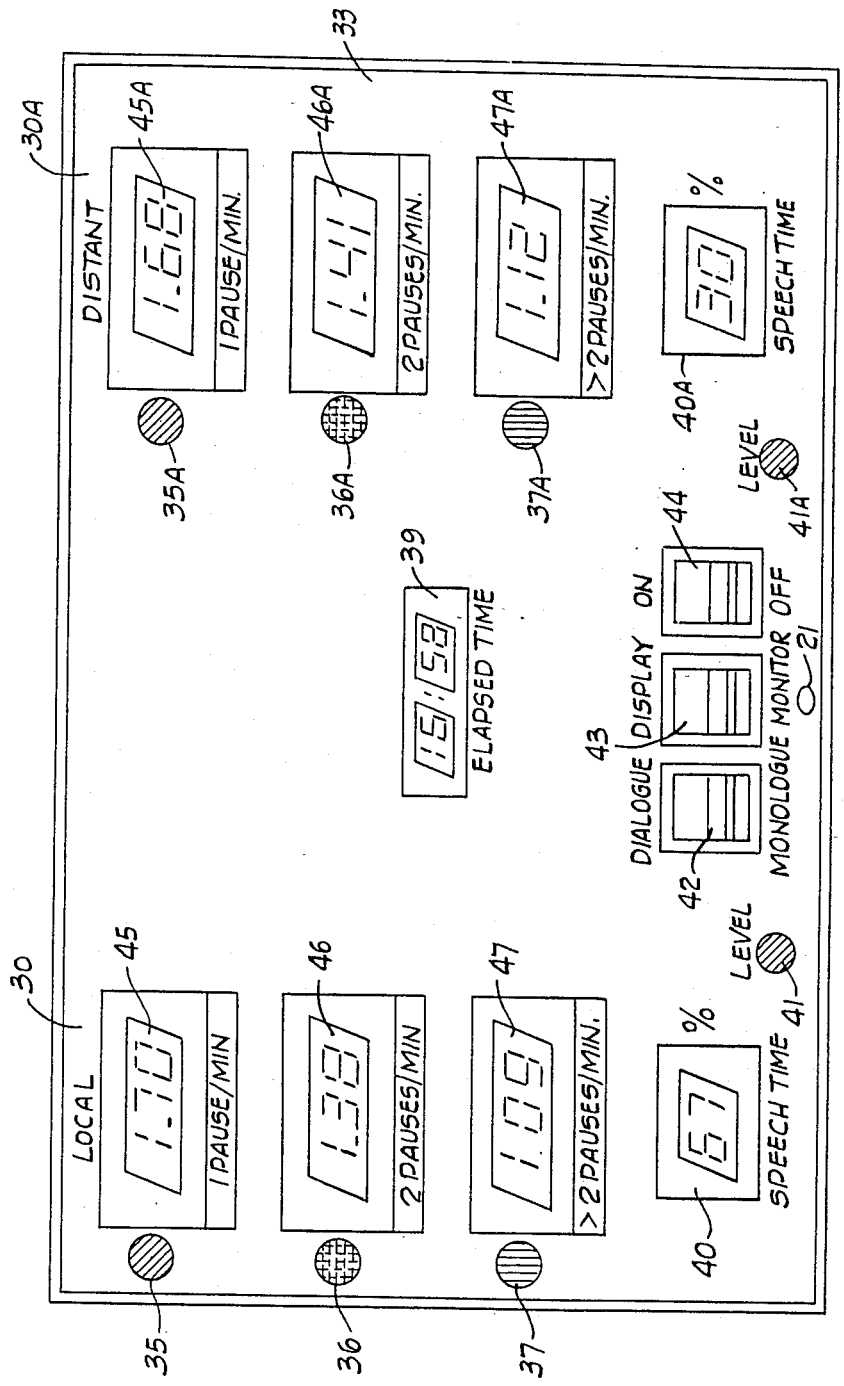
FIG. 2 is a plan view of the front panel of apparatus embodying the invention.

FIG. 1 illustrates a block diagram of the present invention, which determines human response and, more particularly, neuromotor response. In one form of the invention, the neuromotor response may permit comparison, either interpersonal or intrapersonal, by means of a dual display, and this dual display is illustrated in FIG. 2.

The neuromotor response apparatus 20 shown in FIG. 1 includes a transducer 21, which may be any form of transducer of the neuromotor response, either an analog or a digital transducer. In this FIG. 1, the transducer 21 is shown as a microphone having an output fed to a voltage amplifier 22 to amplify the signal level, and then it is passed to a comparator 23, which saturates and forms square-topped pulses. This helps to distinguish over interfering noise and makes essentially a pulse train. This pulse train is then passed to a frequency-to-analog converter, shown as a frequency-to-voltage converter 24, and the voltage signal therefrom is passed to a window comparator 25. This window comparator 25 limits band width to the fundamental components of human speech. The signal is passed on a line 26 to a microprocessor 29, which processes the signal in accordance with a predetermined program, and the information is then passed to an output or display unit 30.

The neuromotor response apparatus 20 permits not only a single display or output, but also a dual display or output, and to accomplish this, the elements 21-26, 29, and 30 referred to above are duplicated in FIG. 1, and shown with the letter A suffix. Additionally in FIG. 1, it will be noted that the line 26 feeds not only the microprocessor 29, but also feeds one input of an exclusive NOR gate or digital comparator 27. Line 26A supplies the microprocessor 29A, the microprocessor 29 through a switch 42, and the other input of the exclusive NOR gate 27. The output of this gate is supplied to the microprocessor 29A. This allows the same program to be used by the dual display 30 through logical switching.

FIG. 2 illustrates a display panel 33 which incorporates the output unit as a recording or display unit 30 on the left and a recording or display unit 30A on the right. This particular display panel 33 is adapted for neuromotor responses which are the voices of two persons, namely an interpersonal interaction, and one feature of the present invention is that it may be utilized with a telephone so that the display unit 30 displays the local voice response and the display unit 30A displays the distant voice response. It may also be used with other interpersonal communication, e.g., units such as keyboard units with the local keyboard inputs displayed on the left and the distant keyboard inputs displayed on the right. Still further, it may be utilized for intrapersonal interaction, e.g., neuromotor response of actuation of pedals on a motor vehicle or vehicle simulator, with the left foot neuromotor response displayed on the left display panel 30 and the right foot neuromotor response displayed on the right half display 30A. It may be used also as a single display of manual movement hiatuses of a writing instrument, of responses to a steering wheel of a motor vehicle or vehicle simulator, or a dual display of responses to a motor vehicle steering wheel plus responses on a vehicle pedal, e.g., the accelerator.

The present apparatus is capable of determining the occurrence of a hiatus or hesitation pause in the human or neuromotor response of a subject, and this is defined as the absence of all monitored human or neuromotor responses for a predetermined time interval bounded by the predetermined response. When the response is a voice response, it may be defined as a timed interruption in the response of such subject. The timed interruption may be in the order of one second of time. Also, the apparatus is capable of measuring the average hiatus rate in a given time segment of a response. If, for example, a person is engaged in a dialogue with another person or a computer (either a voice or keyboard dialogue), the number of hesitation pauses in a total conversation will determine the average rate of such hesitation pauses. The apparatus is capable of sorting these hesitation pause rates into at least two levels of fluency, and FIG. 2 shows the display panel 33 as having three different levels or rates of hesitation pauses. A green lamp 35 may be illuminated if the hesitation pause rate is about one pause per minute, or less; a yellow indicator lamp 36 may be illuminated if the hesitation pause rate is between about one and two pauses per minute; and a red indicator lamp 37, as part of an output indicator 38 (FIG. 6), may be illuminated if the hesitation pause rate is in excess of about two pauses per minute. Similar green, yellow, and red indicator lamps 35A, 36A, and 37A are provided on the right half display unit 30A. An elapsed time indicator 39 is provided to indicate the time of the entire communication. A present speech time indicator 40 and 40A indicates the percentage of the total time that each of the two individuals is speaking or communicating. A green level indicator lamp 41 is illuminated if the local voice is speaking loudly enough so that a microphone transducer 21 obtains a satisfactory input level. A similar green indicator lamp 41A for the distant voice indicates whether a satisfactory signal level is being received from such distant voice. Switches 42, 43, and 44 are also provided on the display panel 33 to control a dialogue/monologue mode, a display/monitor selector switch, and an ON/OFF control.

The green, yellow, and red indicator lamps 35, 36, and 37 provide a sensory output of satisfactory, caution and unsatisfactory rates of hesitation pauses in the communication of each of the two persons. Additionally, juxtaposed to these indicator lamps are green, yellow, and red digital readouts 45, 46, and 47, respectively. These give a sensory output to the eye of the observer of the average duration of the hesitation pauses in each of the three levels or rates of hesitation pauses. Similarly, green, yellow, and red digital readouts 45A, 46A, and 47A are juxtaposed to the green, yellow, and red indicator lamps 35A, 36A, and 37A, respectively, for a similar purpose.

Figure 3:
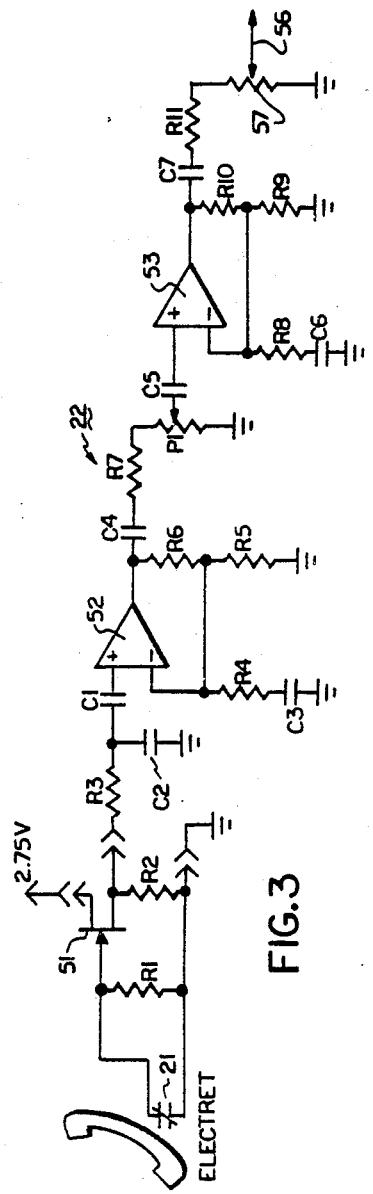
FIG. 3 is a schematic diagram of a preferred voltage amplifier circuit for a microphone pickup.

FIG. 3 illustrates a portion of the neuromotor response apparatus 20 in a preferred embodiment of a voice responsive apparatus. More specifically, FIG. 3 illustrates the voice amplifier section 22 shown in the block diagram of FIG. 1. This voice amplifier 22 has an input from the transducer 21, which in this case may be a microphone such as an electret microphone having a capacitive effect. This may be close to or away from a telephone 62. The signal is buffered by an FET transistor 51, and further amplified in operational amplifiers 52 and 53. The electret microphone does not have a high level output, so several stages of gain are desirable, and each stage acts as a filtering stage in addition. This means that the voice signal changes from complex sine waves with harmonics to one which is more nearly a rectangular wave by the amplifying the clipping action of these several amplifier and filter stages. The signal, at an output conductor 56 at the end of the chain of amplifiers is , supplied to terminal 59 in FIG. 4 for further filtering. Potentiometer 57 provides gain adjustment.

Figure 4:
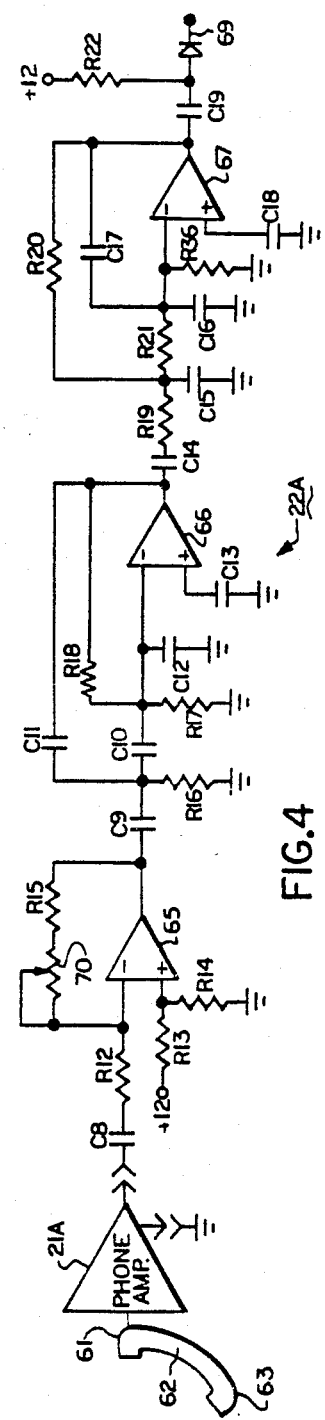
FIG. 4 is a schematic diagram of a preferred form of a voltage amplifier circuit and band pass filter.

FIG. 4 is a schematic diagram similar to that of FIG. 3, and illustrates the circuit which may be used in the voltage amplifier 22A of FIG. 1 when such voltage amplifier is used with a voice responsive circuit. The circuit of FIG. 4 may be utilized with a telephone, with the transducer or microphone 21 responsive to the local voice and transducer 21A responsive both to the remote voice and the local voice. In FIG. 4, this transducer 21A is shown as a phone amplifier located adjacent to the earpiece 61 of a telephone 62. The mouthpiece 63 of this telephone 62 would receive the local voice, and this local voice would actually be received both in the microphone 21 on the display panel 33 of FIG. 1 and on the phone amplifier 21A adjacent the earpiece 61. This reception of the local voice signals on both the microphone 21 and the phone amplifier 21A, reception of only the remote voice signals on the phone amplifier 21A, with noise on both yet discrimination between the two voices, is accommodated by the present neuromotor response apparatus 20.

In the voltage amplifier 22A, the phone amplifier 21A supplies a signal which is amplified by Op/Amp 65, and with Op/Amps 66 and 67 acting as a band pass filter of 300 to 3000 Hz for both channels. The Op/Amp 67 supplies an output conductor 69 and is controlled in gain by a potentiometer 70. Again, the two Op/Amp stages act as combined filtering stages, so that essentially a pulse train output is presented to the output conductor 69 at a voice frequency.

FIG. 5 illustrates schematically the components of the comparator 23, frequency-to-voltage converter 24, and window comparator 25 shown in FIG. 1. The circuit of FIG. 5 is duplicated in FIG. 1 so that the same type of components are used for the parts 23A, 24A, and 25A. FIG. 5 shows an input conductor 71 which will receive an input from either channel via the output conductor 69. This input conductor 71 supplies a signal to an Op/Amp 72, which is the type of Op/Amp which has an open collector and is configured as a comparator in its comparing with an offset from ground level. The output of this Op/Amp 72 is truly a square-topped pulse train signal at a frequency which includes the voice range of 300 Hertz to 3 kilohertz. The output is fed to a frequency-to-voltage converter 24, which has an output at 73 and 74 to the window comparator 25. This window comparator comprises Op/Amps 75 and 76. The purpose of the window comparator is noise rejection to obtain a sharp cut-off band pass filter, between 300 and 3000 Hertz, for example. A pull-up resistor 77 is connected to a positive voltage source and feeds through a resistor 78 to a normally biased on transistor 79, which gives a low true output on conductor 80, referring to negative logic, because of the pull-up resistor 81. If no voice signal is present on the input conductor 71, there is a zero volts signal on the output conductors 73 and 74, and Op/Amp 76 is biased on by resistors 82, 83, and R33 to act as a current sink for the pull-up resistor 77, thus turning off transistor 79 and making the output conductor 80 a high false condition under negative logic. This is also true if some signal occurs which is less than 300 Hertz, with Op/Amp 76 on, or higher than 3000 Hertz, with Op/Amp 75 on, so that it is assumed to be noise rather than voice, and hence the circuit is highly noise-rejecting. However, when a voice signal does appear on the input conductor 71, the window comparator 25 is biased off into a non-current sinking condition on both comparators 75 and 76, the pull-up resistor 77 thus turning on transistor 79 for a low true condition on output conductor 80. The level indicator lamp 41 is connected for energization through a transistor 79A, which is essentially in parallel with transistor 79, to be illuminated when there is a voice signal present.

The circuit of FIG. 1 is duplicated, one for the microphone 21 and one for the phone amplifier 21A. As stated above, when the local person is speaking into the mouthpiece 63, that voice signal is picked up both by the microphone 21 on the display panel 33 and by the phone amplifier 21A; thus, on the output conductor 80 for each of the two circuits, there will be a signal. However, when the distant voice is speaking, only the phone amplifier 21A will receive a signal and will provide an output on only that output conductor 80 of the phone amplifier 21A. Thus, the present neuromotor response apparatus 20 is one which conditions the microprocessor 29 to determine whether this is a local or distant voice, as per Table 1 which follows.

TABLE I

| Test Subject | μP Decode | Dialogue Local | Dialogue Distant | Monologue Local |
|---|---|---|---|---|
| Talking | Local | $\overline{A} \cdot \overline{B}$ | $\underline{A} \cdot \overline{B}$ | $\overline{A} \cdot \overline{B}$ |
| Listening | Distant | $\underline{A} \cdot B$ | $\underline{A} \cdot B$ | NV |
| Noise | Noise rejection | $A \cdot B$ | $A \cdot B$ | NV |
| Pause | Pause | $A \cdot B$ | $A \cdot B$ | $A \cdot B$ |

In Table 1 a truth table is set forth for each of dialogue local, dialogue distant, and monologue local. In this truth table, the letters "A" and "B" have been used, since each microprocessor 29 and 29A has been programmed identically, and the two inputs on $T_0$ and $T_1$ represent two different persons—the local and distant voice, respectively—for the microprocessor 29, and because of the exclusive NOR gate 27, they represent the distant and local voices, respectively, for the microprocessor 29A. The microprocessor performs the decoding of the truth table, as set forth in Table 1. For example, under the dialogue, local voice, the truth table sets forth $\overline{A} \cdot \overline{B}$. Because this is negative logic, the low true signal of each of these input signals on the terminals $T_0$ and $T_1$ indicates that the local voice is talking. The next item in this column indicates that the local voice is listening, which is the case whenever the distant voice is speaking. The third item in this column is some spurious signal or noise, and hence the microprocessor rejects this condition. The fourth item in the column is the only thing that is recorded as a pause, and this is when both A and B are high false, using negative logic, indicating an absence of signal on both input terminals $T_0$ and $T_1$. The truth table for the distant voice during a dialogue has the same two conditions as the local voice during a dialogue for the last two items in the two columns, yet it will be noted that the A signal is reversed for the first two items in the distant column relative to the local column. By this means, a single program may be used for the two microprocessors 29 and 29A.

The system of FIGS. 1–5 may also be used for two persons intercommunicating by voice when face-to-face, as seated across a table, rather than communicating by telephone. In such case, the transducer means would include two microphones, preferably in a single mount so as to be positioned closely adjacent and back-to-back. These microphones could be in the center of the table and facing the respective person. Also in such case, there would be used two of the circuits of FIG. 3 rather than one each of the circuits of FIGS. 3 and 4. Since the circuit distinguishes between the two voices, it prevents cross talk between the two microphones, even though they are mounted in the same housing.

The front panel of FIG. 2 shows the results of the human response system. No indicator lamps 35, 36, or 37 are illuminated if the pauses per minute are equal to zero. The red LED lamp 37 is illuminated if the pauses per minute are greater than two. The yellow LED lamp 36 is illuminated if the pauses per minute are between 1.49 and 2 per minute. The green LED lamp 35 is illuminated if the pauses per minute are between zero and 1.50 (which is in the order of one pause per minute). Thus, the dominant or average frequency level of the hesitation pauses is indicated by the illumination of the respective lamps 35, 36, and 37.

Figure 8:
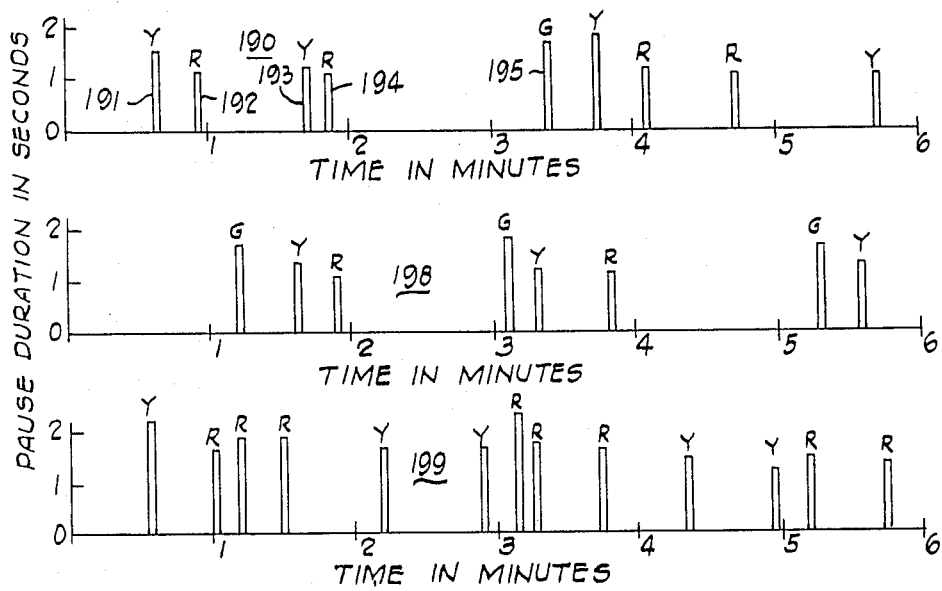
FIG. 8 is a graph of representative pause durations relative to time.

FIG. 8 shows several graphs of pause durations plotted against the time of the dialogue. Graph 190 shows a graph of the hesitation pauses of the subject A as displayed for the local voice of FIG. 2. In this particular example, the hesitation pause is defined as an absence of vocal sounds uttered by the subject, bounded by the speech of the subject, and having a duration of one second or more. Therefore, all of the pauses in Graph 190 have a pause duration of one second or more. Each of the pauses has a letter G, Y, or R above it to indicate whether it is a green, yellow, or red code pause. The first pause 191 is a yellow code pause, because it has occurred at less than one minute of time of the dialogue with the distant voice, such as a doctor or interviewer, and therefore the pause rate is greater than one per minute. The next pause 192 is a red code pause because it has occurred at less than one minute of the dialogue, and hence the rate is greater than two pauses per minute. The third pause 193 is assigned a yellow code because in the preceding one minute there was only one other pause, namely pause 192. The fourth pause 194 is assigned a red code because in the preceding one minute there were two other pauses. The next pause 195 is assigned a green code because in the preceding one minute there were no other pauses. The remaining pauses in this Graph 190 are assigned a code by the same criteria. The result is shown for the local voice in FIG. 2, namely, the average pause duration for the green code pauses (in this case only a single pause) was 1.70. The average pause duration for the yellow code pauses was 1.38 and the yellow indicator lamp 36 would be illuminated because there was a total of nine pauses in slightly less than a six-minute dialogue; thus, this is at a rate greater than 1.5 pauses per minute and less than two pauses per minute. The average duration of the red code pauses was 1.09, again as displayed for the local voice on FIG. 2. A red light in the local voice and a green light in the distant voice indicates a discrepancy of 0.59 seconds or a failure of harmony based on dominant mode duration alone. In addition, the greater dysrhythmia of the local voice further adds to discordance. Significantly shorter pauses by the local voice suggest speech may be too rapid, in addition to being dissonant, for the distant voice to assimilate what is being said. This would be even more likely if the distant voice were more poorly adapted with dysrhythmic speech, e.g., red mode at 1.68 seconds.

Graph 198 in FIG. 8 displays the distant voice pauses in duration and at time locations during the dialogue with the subject A. In Graph 198, there are eight pauses, which have been assigned a green, yellow, or red code in the same manner as those assigned for Graph 190. The average pause duration of the three green code pauses is 1.68, and the green indicator lamp 35A would be illuminated because there are only eight pauses during the approximately six-minute dialogue; hence, this is at a pause rate of less than 1.49 pauses per minute. The average duration of the yellow code pauses is 1.41 and the average duration of the red code pauses is 1.12. This is as displayed on the distant voice section of FIG. 2. Also, FIG. 2 shows that the subject A utilized 67% of the total speech time, and the distant voice B utilized 30% of the speech time. These two graphs illustrate that the distant voice had better prosody than the subject voice in having a greater number of green pauses and a fewer total number of pauses, so that the green indicator lamp 35A was illuminated, whereas, for the subject voice the yellow indicator lamp 36 was illuminated, indicating a greater number of pauses. The subject had a desirable increase of pause duration from red to yellow to green, as shown by the increased pause duration on the display panel 30. The interviewer also had the same desirable increase in pause duration from red to yellow to green, and further had greater prosody and the best correlation between pause duration and pause rate because the green indicator lamp was illuminated, indicating a desirable low rate of pauses. Further, the interviewer attempted to maintain high fluency while matching the subject in his hesitation pause duration, thus establishing a good rapport with the subject and a reassuring dialogue. This can be quite important where the interviewer is a doctor speaking on the telephone to a subject who might be under severe depression or have suicidal tendencies.

Graph 199 of FIG. 8 is a graph of the hesitation pauses in a dialogue of a subject who is more hesitant than the subject of Graph 190. Again, the various pauses have been assigned a red or yellow code, and since there was no minute during the dialogue when there was not at least one hesitation pause, none of the succeeding pauses was assigned a green code. Therefore, in the display of the green, yellow, and red pause durations on the display panel, there would not be any digital display of pause duration for the green code pauses. The yellow code pauses would average about 1.66 and the red code pauses would average about 1.76 seconds in duration. Also, the red indicator lamp 37 would be illuminated because a total of 13 pauses in the less than six minutes of dialogue would be a pause rate greater than two pauses per minute.

When a subject views the display panel of FIG. 2 and notes that his red code light 37 or 37A is illuminated, the display panel has the green level lights 41 and 41A illuminated, as is usually the case, and also the other person's green indicator lamp 35 or 35A is illuminated. He will observe his red light framed by green lights. This framing of red by green light enhances a person's perception of his own red light, and hence awareness of his being in a red or unsatisfactory code. The opponent cells in the visual cortex are the physiological basis for this light-framing configuration.

Figure 7:
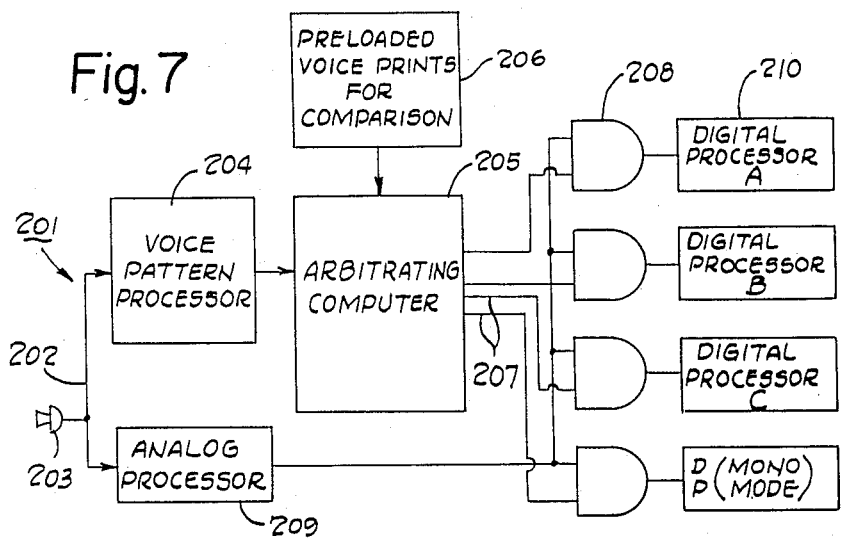
FIG. 7 is a block diagram of a modification utilizing a voice print comparator.

FIG. 7 illustrates a modification wherein a neuromotor response apparatus 201 of a modified form is shown. In this case, more than two persons may utilize the apparatus. An audio input is supplied on line 202 from a suitable source such as an omnidirectional microphone 203, and which could be used in a classroom, for example, having an instructor and several students. The line 202 conducts the audio signal to a voice pattern processor 204, whereat the voice of that particular person speaking is processed, e.g., digitally, and directed to an arbitrating computer 205 whereat it is compared with the preloaded voice prints from a memory unit 206. Such memory unit of preloaded voice prints would have been pre-established in order to provide in the computer 205 a means to identify the person speaking. The output would then appear on the selected one of a plurality of output lines 207 to one input of a plurality of AND gates 208. The other input of these AND gates 208 would be each connected to the output of an analog processor 209 which would be the circuits of FIGS. 3 and 5 in sequence, for example. Thus, the particular selected output line 207 would enable that particular AND gate and the signal would be passed to the respective one of a plurality of digital processors 210. In this way, there could be a determination and display of the pause duration and pause rate for each person in a large group.

Figure 6:
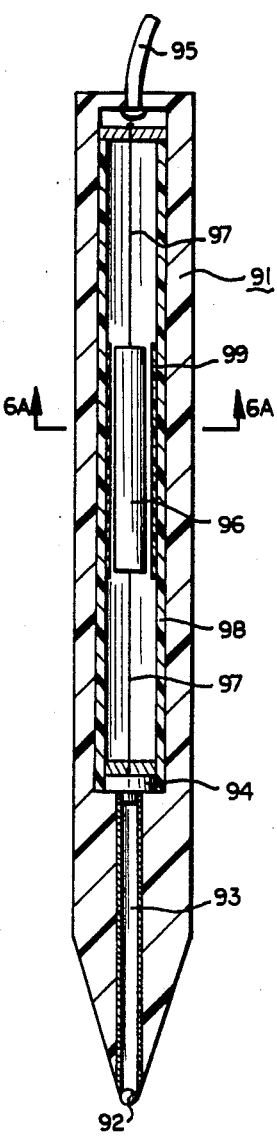
FIG. 6 is a longitudinal, sectional view of a manual writing instrument to determine pauses in writing.
Figure 6A:
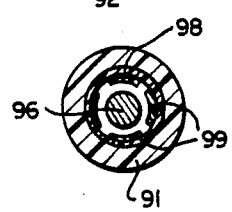
FIG. 6A is a sectional view on line 6A—6A of FIG. 6.

FIGS. 6 and 6A show a manual writing instrument 91 which in this preferred embodiment is shown as having a ballpoint pen 92 and an ink supply 93. When the pen is used for writing, the pressure on the paper is transmitted by the ink supply cartridge to a pressure transducer 94 to provide an electrical signal out of an attachment cable 95 to the neuromotor response apparatus 20. Also, the writing instrument includes an accelerometer which includes a mass 96 supported by taut nylon filaments 97 inside a tube 98. At four different sectors on the inner wall of the tube there are provided films 99 adapted to be contacted by the mass 96 whenever the writing instrument is accelerated in any lateral direction. These films are piezoelectric so that they develop a voltage signal upon being contacted by the mass. These piezoelectric films may be made from polyvinylidiene fluoride. The signal from this accelerometer may be passed to the electrical attachment cable 95 to the neuromotor response apparatus 20. This writing instrument 91 may be utilized to determine the hiatuses or pauses in writing by using the pressure transducer as the transducer input to the neuromotor response apparatus. The signal from the accelerometer establishes that the ON-OFF signal from the pressure transducer is a valid signal during writing. Typically, when one is signing his name, there are one or more pauses in that signature, even though it is a very customary occurrence to sign one's signature and is performed by rote. At least one pause is usually between the first and last names of the signature. The writing instrument 91 is an example of using the neuromotor response apparatus 20 for non-language motor activity. Motor cortex in the frontal lobes slightly posterior to Broca's Area are the anatomic substrate for contralateral leg and arm movements, such as in the operation of a motor vehicle and for hand functions utilized in writing. These complex tasks require complementary actions of the left and right hemispheres. The prior U.S. Pat. No. 3,983,535 discloses apparatus for signature verification based on pen pressure and acceleration. The present invention permits the inclusion of the pauses in writing to be utilized. This has the potential of increasing the accuracy of signature verification. The pressure transducer 94 can determine the beginning and ending of the period of time for writing the signature, with the accelerometer monitoring when the pressure transducer signal is valid, and also can determine the length of each of the individual pauses during writing a signature. The hand-brain-hand processing time in signature writing is in the order of 100 milliseconds. In this use of the writing instrument, interhemispheric transmission time measured as the difference between hiatus times at more than four hiatuses per minute (red light) and four or less hiatuses per minute (yellow light) is estimated to be in the order of two to six msec. The accuracy of signature verification would be improved by a pause profile wherein pause times in writing in excess of 100 msec were sorted at two or more frequency levels on a time base. For example, it has been noticed that certain individuals, such as artistic types, write the first letter of their first name with a flourish, then pause and write the balance of their signature without stopping. Some do stop, for a shorter time than the first pause, between the first and second name. Thus, the ratiometric comparison of the length of the first pause divided by the length of the second pause would be a constant over time. In both of the above cases, writing is farily fluent, with the first case showing a green light, whereas, the second case might show a green or yellow light, depending upon the spacing of the pauses on the time base. Individuals who are customarily in the red light mode typically have a very long pause between their two names compared with shorter pauses within each of their names. Therefore, ratiometric comparison has utility for accuracy enhancement with these individuals as well, since, while the absolute pause duration may vary over time with their fatigue levels, etc., the ratios are likely to remain constant.

Hiatuses or pauses in writing one's signature are similar to the hiatuses in a person's voice, because both are part of the generic approach to language as an intercommunication medium. Therefore, these hiatuses are a valid measure of human response whether in a signature verification pen or a voice fluency monitor. The ratiometric method also can be applied to the comparative analysis of within-word speech pauses to provide a fourth level of understanding speech in addition to waveform and amplitude of syllables (U.S. Pat. No. 4,519,094), grammatical construction of sentences, and word content.

Figure 9:
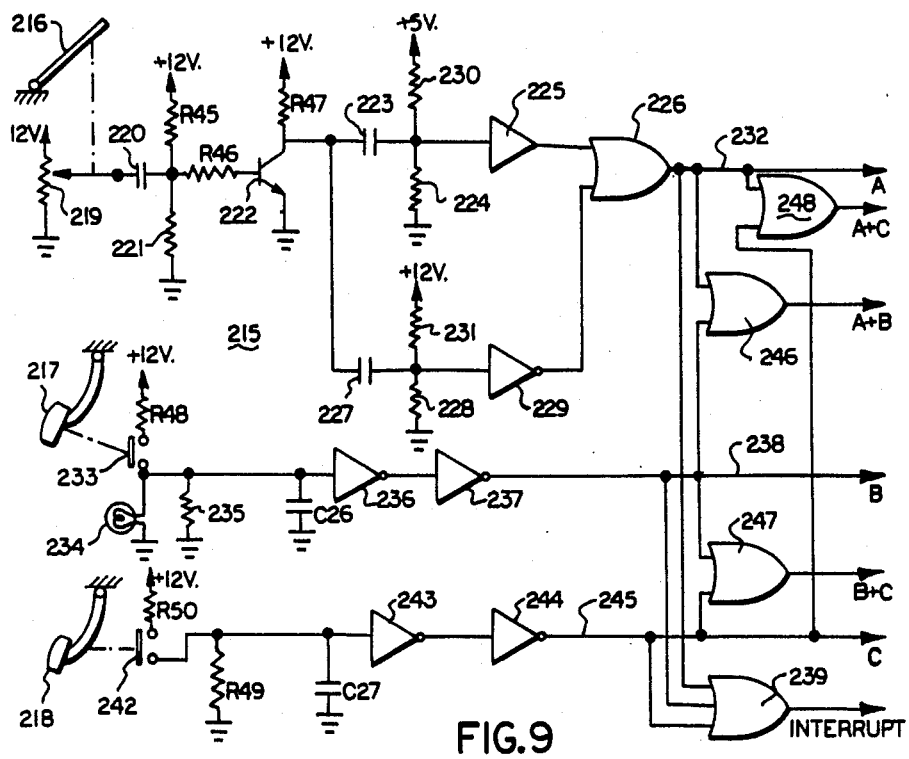
FIG. 9 is a schematic diagram of a modification determining response of pedal actuation in a motor vehicle.

FIG. 9 is a modification showing a neuromotor response apparatus 215, in this case responsive to the pedal action or foot response of a subject. The apparatus 215 is an intrapersonal response apparatus responsive to only a single person but with the possibility of a dual, triple, quadruple determination and display of the response of the hands and the left foot and right foot of such person. The apparatus 215 is adapted to be used with a motor vehicle or vehicle simulator having a steering wheel, an accelerator 216 and a brake pedal 217. It is therefore suitable for a vehicle with either an automatic or manual shift transmission. In the latter case, the vehicle or simulator will also have a clutch pedal 218. The accelerator pedal 216 is linked to the movable element of a potentiometer 219, and passed through a differentiator consisting of a capacitor 220 and resistor 221, so that a slight change in the accelerator pedal setting produces a sharp spike which adds or subtracts from an average bias level of about six volts. This is amplified in a transistor 222, and then passed to a pair of differentiators. The first differentiator includes a capacitor 223 and resistor 224, then to a buffer gate 225 and then to an OR gate 226. The second output of transistor 222 passes to a differentiator which includes capacitor 227 and resistor 228 with a signal passed to an inverter gate 229 and thence to the OR gate 226. The spike on the input of the transistor 222 is amplified to become a pulsatile wave, either positive or negative on the output thereof. The buffer gate 225 is biased just below the threshold by means of a resistor 230 and the resistor 224, and hence passes only the positive going pulsatile wave signals to the OR gate 226. The inverter gate 229 is biased just above the threshold by a resistor 231 and the resistor 228 so that it passes only the negative going pulsatile wave signals to the OR gate 226. The inverter gate 229, of course, inverts the signals so that they are positive going, the same as the signals coming from buffer gate 225. Thus, on the output line 232, accelerator signals will be present, giving a positive logic true signal for any slight movement of the accelerator toward either increased or decreased speed.

The brake pedal 217 may actuate a separate electrical momentary closed switch, but for convenience may operate from the brake light switch 233 to actuate a brake light 234. An optional resistor 235 may be connected to ground in parallel with the brake light in case this brake light filament burns out. The signal from the brake light switch 233 passes through two inverter gates 236 and 237 to obtain double inversion for buffering and level shifting. The signal of actuation or deactuation of the brake pedal 217 thus appears on the output line 238, and this may be considered the B signal input to the microprocessor on the circuit of FIG. 1. The signal from the accelerator output line 232 may be considered the A signal, again to such microprocessor of FIG. 1. These two signals on lines 232 and 238 are connected on inputs to an OR gate 239, and the output thereof supplies an interrupt signal to alert the microprocessor.

Where the apparatus 215 is to be usable with a vehicle with a manual shift transmission, having the clutch pedal 218, a clutch actuation signal is provided. The clutch pedal is connected to actuate a momentary close switch 242 as the clutch disengages. The signal from switch 242 passes through two inverter gates 243 and 244 and appears on output line 245. This line output may be considered a C signal, again to a microprocessor of FIG. 1. That line is also connected to an input of the OR gate 239 for an interrupt signal. OR gates 246, 247, and 248 are connected across the pairs of output lines 232,238; 238,245; and 232,245 to provide additional inputs to microprocessors of FIG. 1 of A or B; B or C; and A or C. The accelerator response microprocessor, such as the one in FIG. 1, would have the input at $T_0$ from the accelerator signal A, and the input at $T_1$, from the B+C signal from OR gate 247. The brake response microprocessor would have the $T_0$ and $T_1$ inputs from the brake signal B and the A+C OR gate 248, respectively. The clutch response microprocessor would have the $T_0$ and $T_1$ inputs from the clutch signal C and the A+B OR gate 246, respectively.

This circuit preferably would not display the information while the motorist was driving or being tested on a vehicle simulator, but would display it only upon turning off the ignition switch, thus avoiding distracting the driver during the trip or test. Display of the information could be on a display panel such as panel 33 in FIG. 2. The accelerator actuations, either positive or negative, would be displayed on the local display panel 30 and the brake actuations would be displayed on the distant panel 30A. A third display panel, similar to the other two, would display the clutch actuations. A fourth display panel could display the steering wheel events. Five registers would be used for the dual display and at the trip termination, these registers would yield data as follows: (1) the total trip time; (2) accelerator-to-accelerator events; (3) brake-to-brake events; (4) accelerator-to-accelerator total time; and (5) brake-to-brake total time. Where the triple display was utilized, additional registers would yield data on: (6) clutch-to-clutch events; (7) accelerator-to-clutch events; (8) clutch-to-accelerator events; (9) brake-to-clutch events; and (10) clutch-to-brake events. In a quadruple display, additional registers would yield data on the accelerator, brake, and clutch interaction with the steering wheel. By extending these registers, time and events could be stored as those falling within a plurality of time interruption rates for display in the three digital readouts 45, 46, and 47 on the display panel 33. Final computation would divide the event time by the event number, yielding the average time per event.

Figure 10:
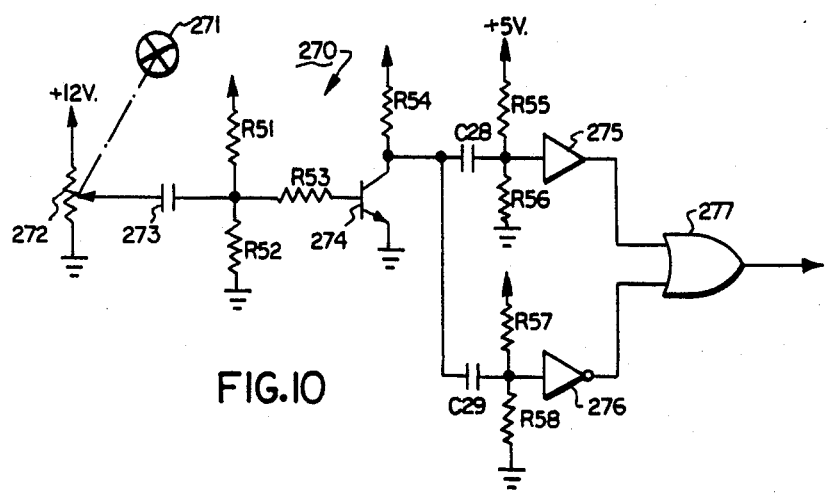
FIG. 10 is a schematic diagram of a modification determining steering wheel response in a motor vehicle.

FIG. 10 illustrates schematically the neuromotor response apparatus 270, wherein a steering wheel 271 is moved by a neuromotor response, namely, the movement of the hands of the vehicle operator. The steering wheel 271 is connected to the movable element of a potentiometer 272 in a circuit which is similar to the neuromotor response apparatus 215 of FIG. 9. The potentiometer is connected across the vehicle voltage source, such as 12 volts, so that as the steering wheel is moved, a signal is passed through a capacitor 273 and amplified by transistor 274 as either a positive going or negative going pulse, which is passed by a buffer gate 275 or an inverting gate 276, respectively, to an OR gate 277. Thus, movement to the right or left of the steering wheel 271 produces a pulse output from the OR gate 277. This signal is passed to the microprocessor, similar to that shown in FIG. 1. The microprocessor outputs may go to the output unit 30 of FIG. 1, which, for example, can be a display unit as shown in FIG. 2 to activate the red, yellow, or green lamps 35, 36, and 37.

Figure 11:
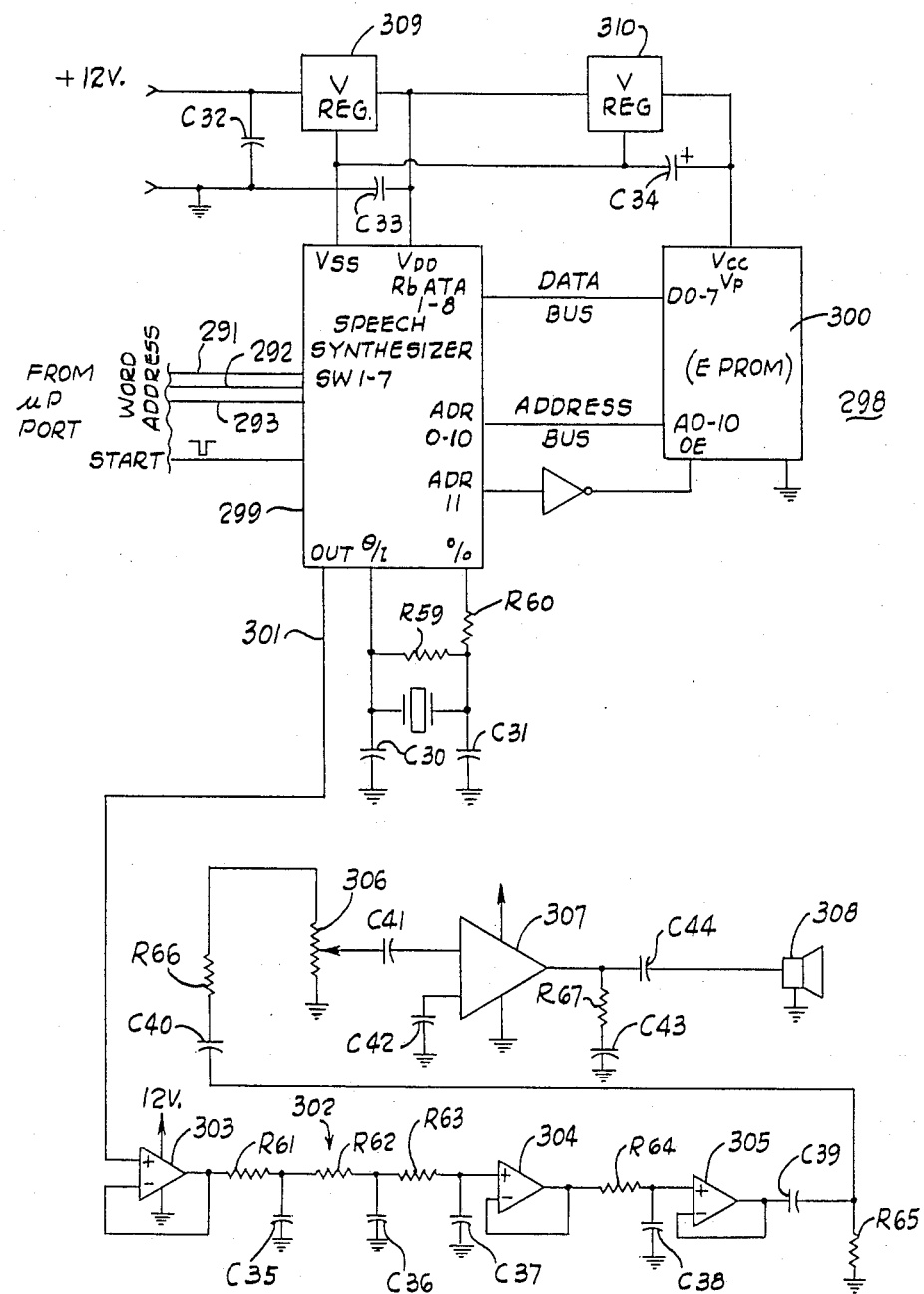
FIG. 11 is a schematic diagram of a speech synthesizer controlled by the output of the microprocessor.

Alternatively, the red, yellow, or green output lines 291, 292, and 293 of the microprocessor may be passed to a voice synthesizer circuit 298 shown in FIG. 11. These three output lines 291, 292, and 293 are connected to switch inputs of a speech synthesizer module 299. An EPROM 300 would be previously encoded with a number of digitally encoded messages such as "Easy on the clutch," "Please slow down for fuel efficiency," "Less frequent use of the brake gives better fuel economy," "Fewer steering movements provide a more comfortable ride," "Riding the clutch or brake causes unnecessary wear," etc. The speech synthesizer module 299 forms speech from this digitally encoded message putting the proper inflection, timing, frequency and pitch to the various combined syllables to make intelligible speech. This is passed on the output line 301 through a digital filter 302, which includes Op Amps 303, 304, and 305, with the signal then passed to a volume control 306, which is then amplified by a power amplifier 307. This supplies a loudspeaker 308. Voltage regulators 309 and 310 supply the regulated voltage to the module 299 and EPROM 300. By this circuit 298, the caution or unsatisfactory codes may be imparted to the subject, e.g., the driver of an automobile, by the synthetic voice rather than by some visual display which might distract the driver. The EPROM 300 can be digitally encoded with voice messages, which are interpreted by the left hemisphere of the brain of the driver. The EPROM 300 can also be encoded with a tuneful melody, either first or as background music to the voice messages, and this will have a positive reaction to the right brain hemisphere, for a balance of brain hemisphere input, and so that the voice message will be more acceptable to the driver. This entire circuit shown on FIG. 21 may be purchased from National Semiconductor, mounted on a printed circuit board.

The neuromotor response apparatus 20 may also be utilized in other ways to determine hiatuses or pauses in neuromotor response. For example, it may be used in a helicopter simulator or training device in which a simulation of a scene which a helicopter pilot might see out of his windshield is flashed onto a large screen in front of the trainee in the helicopter simulator. Also close in front of the trainee's right eye, a semi-transparent small screen is placed on which are projected possibly threatening situations. The pilot trainee can respond by voice and also respond by hand and foot movements on the controls of the helicopter simulator. It has been determined that the interhemispheric transmission time at the occipital site is in the order of 14 to 16.6 milliseconds. This is the time required for focal visual attention, which requires coordinated bilateral occipital hemisphere functions reflected in intact callosal transmission. For example, when a helicopter pilot is subjected to real world scenes on the simulator by video tape or laser disc cassette presentation, those visual stimuli would be expected to elicit the above values of interhemispheric transmission times calculated as the difference between hiatus times at higher and lower rates.

Figure 12:
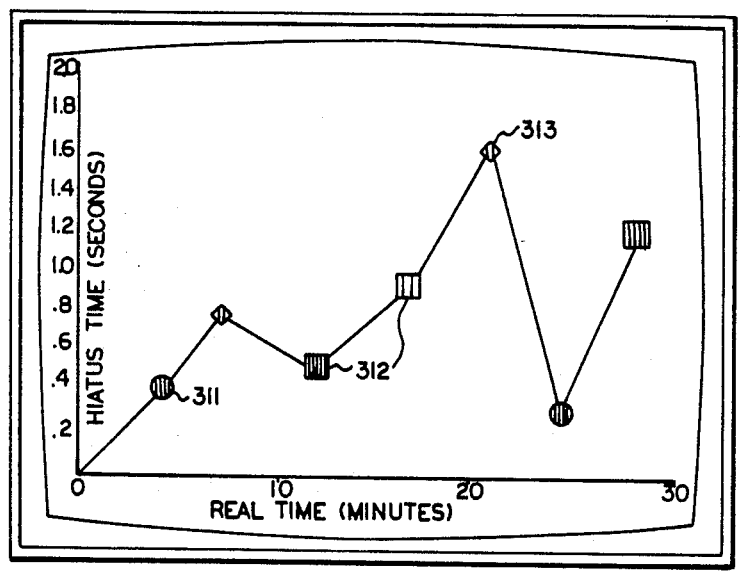
FIG. 12 is a front elevational view of a cathode ray tube which can be used as a display.

Further, an oscilloscope or other video presentation as shown in FIG. 12 may be used as the display 30 of FIG. 1. This display might be one which displays real time in minutes along the abscissa and the hiatus time in second along the ordinate. This would result in rows of dots in a line or curve sloping generally upwardly to the right, but in the practical case is often a sawtooth line. The neuromotor responses of more than one person could be displayed at one time, with the conversational partner's dots marked differently from the first person's dots, for example, with an X through the center of the circle, square or diamond. If the dots were illuminated green, this would indicate one or fewer than 100 msec hiatuses per minute. If the dots were illuminated yellow, this would indicate in the order of two 100 msec. hiatuses per minute. If the dots were illuminated in various shades of red, from pink to clear red (shown in FIG. 12 by hatch lines more closely spaced as the color approaches clear red), this would indicate from three to ten 100 msec hiatuses per minute, respectively. The circles 311, squares 312, and diamonds 313 reflect different levels of environmental challenge on a time base. In the case of the helicopter simulator, this could be the level of three-dimensional challenge, and in the case of a dialogue it could represent the interruptive, loudness or other abrasive voice characteristic of the conversational partner.

Within-word pauses monitored on a time base, i.e., the elapsed time of the spoken word, have the potential to increase the accuracy of word identification which is presently based on vocal tract characteristics and differences in loudness of syllables as described in U.S. Pat. No. 4,519,094. By comparing normal between-word pauses to within-word pause profiles, the present necessity to artificially exaggerate between-word pauses (Business Week, Sept. 23, 1985, pp. 40-41) can be reduced substantially.

In one practical circuit constructed in accordance with the invention generally as shown in FIGS. 1-12, the circuit components and values therefor were as follows:

| Resistance | Value | Resistance | Value |
| --- | --- | --- | --- |
| R1 | 100 Megohms | R46,R47 | 10 Kilohms |
| R2 | 1 Kilohm | R48,R50 | 12 Kilohms |
| R3 | 560 Ohms | R49 | 10 Kilohms |
| R4 | 39 Ohms | R51,R52 | 220 Kilohms |
| R5 | 2.2 Kilohms | R53,R54 | 10 Kilohms |
| R6,R7 | 10 Kilohms | R55,R58 | 220 Kilohms |
| R8 | 39 Ohms | R56,R57 | 100 Kilohms |
| R9 | 2.2 Megohms | R59 | 1 Megohm |
| R10,R11 | 10 Kilohms | R60 | 1.5 Kilohms |
| R12 | 4.7 Kilohms | R61 | 9.1 Kilohms |
| R13,R14 | 10 Kilohms | R62 | 2.2 Kilohms |
| R15 | 150 Kilohms | R63 | 22 Kilohms |
| R16 | 47 Kilohms | R64,R65 | 7.5 Kilohms |
| R17 | 62 Kilohms | R66 | 10 Kilohms |
| R18 | 220 Kilohms | R67 | 10 Ohms |
| R19,R20 | 36 Kilohms | 57 | 50 Kilohms |
| R21 | 18 Kilohms | 70 | 100 Megohms |
| R22 | 330 Kilohms | 77 | 22 Kilohms |
| R23,R24 | 10 Kilohms | 78 | 1 Kilohms |
| R25 | 220 Kilohms | 81 | 5.6 Kilohms |
| R26,R27 | 10 Kilohms | 82 | 5.6 Kilohms |
| R28 | 10 Kilohms | 83 | 680 Ohms |
| R29 | 6.8 Kilohms | 89 | 4.7 Megohms |
| R30 | 100 Kilohms | 221 | 12 Kilohms |
| R31 | 10 Kilohms | 224,231 | 100 Kilohms |
| R32 | 68 Kilohms | 228,230 | 220 Kilohms |
| R33 | 18 Kilohms | P1 | 50 Kilohms |
| R34,R35 | 1 Kilohms | P2 | 10 Kilohms |
| R36 | 15 Kilohms | 219 | 100 Kilohms |
| R42 | 120 Ohms | 235 | 10 Kilohms |
| R45 | 220 Kilohms | 272 | 100 Kilohms |
|  |  | 306 | 50 Kilohms |

| Capacitor | Value | Component | Type |
| --- | --- | --- | --- |
| C1 | 0.1 microfarad | phone amp 21A | RS 43-238 |
| C2 | .001 microfarad | op amp 52,53 | LM 387N |
| C3 | 10 microfarad | op amp 65 | LM 307N |
| C4,C5 | .1 microfarad | op amp 72,75,76 | LM 339 |
| C6 | 10 microfarad | F/V 24 | LM 331 |
| C7 | .1 microfarad | µP 29 | INTEL 8748-8 |
| C8, | 2 microfarad | Display 45-47 | HP 5082 7433 |
| C9,C10 | 0047 microfarad | Q79, 79A | 2N 4401 |
| C11 | .0047 microfarad | Q222 | 2N 4401 |
| C12 | .01 microfarad | Gate 27 | 14070 |
| C13,C14 | .1 microfarad | Gate 225,275 | CD 4010 |

| | -continued | | |
|---|---|---|---|
| C15 | .0056 microfarad | Gate 229,236,237 | CD 4009 |
| C16 | .002 microfarad | Gate 243,244,276 | CD 4009 |
| C17 | .001 microfarad | Gate 226,239 | 74 C 32 |
| C18,C19 | .1 microfarad | Gate 246,247,248 | 74 C 32 |
| C20 | 500 picofarad | Gate 277 | 74 C 32 |
| C21 | .1 microfarad | Op Amp 303,304,305 | LM 324 |
| C22 | .1 microfarad | Op Amp 307 | LM 386 |
| C26,C27 | 10 microfarad | V. Reg. 309 | LM 7808 |
| C28,C29 | .5 microfarad | V. Reg. 310 | LM 7805 |
| C30 | 20 picofarad | 299 | MM 54104 |
| C31 | 50 picofarad | EPROM 300 | MM 2716 |
| C32 | 22 mf. 25 volt | | |
| C33,C34 | 4.7 mf. 10 volt | | |
| C35,C38 | .1 microfarad | | |
| C36,C40 | .01 microfarad | | |
| C37 | 1000 picofarad | | |
| C39,41,42 | .1 microfarad | | |
| C43 | 0.5 microfarad | | |
| C44 | 250 microfarad 16 volt | | |
| 220,223,227 | .5 microfarad | | |
| 273 | .5 microfarad | | |

It will be seen from the general block diagram of FIG. 1 and the specific modifications of FIGS. 2, 6, 7, 9, 10, 11, and 12, that there is disclosed a neuromotor response apparatus and method which measures neuromotor efficiency at two or more levels by comparing responses of two or more interacting individuals or two or more similar responses by one individual. In the case of vocal fluency of the modifications of FIGS. 2 and 7, the potential uses include organizational development to teach communication skills in staff training, hence evaluating interpersonal interaction. Evaluating handedness in terms of finger dexterity utilizing teletypewriter keys or the like is intrapersonal evaluation. Also, the evaluation of imbalance of neuromotor responses in the steering, acceleration and deceleration of a motor vehicle has utility for driver training in a vehicle or vehicle simulator in the apparatus of FIGS. 9 and 10. This may be used for retrospective evaluation of the driver's performance. It also has implications for developing the driver's contribution to fuel efficiency and limiting use of the brake. When a display panel such as that shown in FIG. 2 is used with the apparatus of FIGS. 9, or 10, the pedal interruptions may be displayed on the left and the acceleration pedal actuations on the right. Also, the display may be a triple unit, with the clutch actuation display on the far left. With a quadruple unit display, the steering wheel movements may also be indicated.

A neuromotor response hiatus may be defined as the absence of all monitored neuromotor response for a predetermined time interval bounded by the predetermined neuromotor response. For the pedals alone, this may be defined as movement of the subject pedal without intervening movement of any other pedal. Including the steering wheel, the hiatus may be defined as movement of the subject vehicle control without intervening movement of any other monitored vehicle control. In this case, the apparatus has utility to serve as a "flight recorder" on a school bus and the like to identify driver error; to measure a driver's mental depression and coronary-prone behavior, e.g., suicide and susceptibility to heart attack. These conditions are manifested by frequent movements of the steering wheel. The apparatus also may be used to assess the driver's contribution to fuel efficiency, i.e., pumping the accelerator and wearing out the brakes prematurely by pumping the brake pedal excessively. Inefficient and potentially hazardous lane jumping would be manifested by frequent movements of the steering wheel. The failure to negotiate a curve properly could be manifested by both frequent and excessively long steering wheel movement. Preferably, the display should be presented only after the trip is completed upon turning off the ignition so as not to distract the driver enroute.

A high hiatus rate, e.g., in a person's voice, can be symptomatic of coronary-prone behavior, which can result in hormonal secretions that can be phasic or pulsatile, which in turn can influence blood glucose and the body's insulin requirement. Thus, in diabetics requiring frequent doses of extra insulin, the unsatisfactory or "red" code could trigger the actuation of an implanted insulin pump, and can provide an immediate beneficial biofeedback to the subject. A usual implantable insulin pump has an existing profile of insulin injection algorithmically built into its memory, which may be modified by different stress levels which are determined by the microprocessor 29. It can be used to modify the dispensing program of the pump.

In the embodiment of FIGS. 1-5, wherein the neuromotor response system is a voice-responsive system, then FIG. 8 shows some possible patterns of hesitation pauses. In the graph 199 of FIG. 8, there are many red code pauses. The green, yellow, and red code pauses may be characterized as satisfactory, caution, and unsatisfactory pause rates or frequency of pauses. The present apparatus introduces a microprocessor method of determining and displaying the frequency and duration of speech pauses considered to be useful in assessing brain hemisphere functions.

Pause or hiatus frequency is mediated by the left hemisphere, while pause duration is mediated by the right hemisphere. Impairment of Broca's Area on the left, such as by stroke, results in frequent pauses, while endogenous depression with psychomotor retardation is manifested by elongated pauses and originates from the right hemisphere.

Coordinated interaction between the left and right brain hemispheres is measured as the ability to decrease the rate of hesitation by varying the duration of pauses. Maximal adaptation is demonstrated by inverse correlation between frequency and duration. This is based on the equation, frequency times duration equals a constant, i.e., a finite amount of pause time is required to collect thoughts adequately.

Varying the cadence of vocal delivery from a few shorter pauses to less recurrent longer pauses imparts rhythm or emotional coloration to speech. The emotional component of speech is called prosody, a function of the right brain. Patients with right brain damage often demonstrate aprosodia, the ability to manage the propositional or left brain component of language but not the emotional component.

Thus, the present invention provides a measure of left brain function at three levels of fluency and of right brain function at three levels. It is hypothesized that a higher degree of prosody is present if there is a stepped increase compared with a stepped decrease in pause duration from low to middle to high frequency. For a person who has suffered depression, the pause pattern might be something like that shown in graph 199 in FIG. 8. Therefore, in order to increase prosody, it would be better for that patient to increase the duration of a pause, to gather his thoughts, and then to be able to speak for a period of time without any pauses. This could increase the number of yellow and green code pauses and decrease the number of red code pauses so that the subject could increase his fluency of speech. If equipment is being used by a cardiac patient, for example, and is being used in the monologue mode by actuating the switch 42 to the monologue position, then a disable switch may be opened to disable the red indicator lamp 37. This disable switch may be located on the rear of the panel, and may be actuated to the OFF position by the doctor, so that the cardiac patient will not know that he is always in the red code rate of pauses. The display driver circuit utilizes cross-point multiplexing, so particular segments of the seven-segment displays are connected in parallel, with the red indicator lamp 37 being the third one in the series before the final return connection to the cathodes. The disable switch is then positioned in this series immediately preceding the red indicator lamp 37. This red indicator disabler switch allows the option to focus solely on prosody, which is appropriate for certain patients who would be unduly intimidated by a red light. Also, the monologue switch 42 will permit a cardiac patient or stroke victim to practice by himself in addition to being able to practice in a dialogue.

Viewing the dialogue as a single unit, cross-prosody is a new term defined as a stepped increase in duration from red to yellow to green utilizing at least one value from each speaker. This encourages collaboration in focused staff training, since both partners' scores are considered in attaining prosody, hence mitigating against a pace one partner might consider terse. Another indicator of interpersonal harmony is a closer approximation of partners' pause durations as efficiency levels increase.

From a review of at least 500 telephone calls using similar apparatus, it has been determined that the mean duration of hesitation pause was 1.5 seconds plus or minus one-third of a second. The individual may vary considerably from this mean or average and the apparatus may be used to establish a basic relationship between a teacher and his class. Students may be sorted into subgroups to match teachers with similarly paced behavior. A slow-paced teacher and fast-paced students will result in restless students; whereas, in the reverse case, the students will fail to get the point. In the monologue mode, a student may use the instrument for self-improvement. With the voice print circuit of FIG. 7, the teacher can monitor his presentation to the class. This may be done also in the monologue mode of FIG. 7, as shown in the last digital processor 210 in the group of digital processors.

The present apparatus and method identify pause durations at high, middle, and low coronary risk, and to match dominant pause durations in the dual display format to determine interpersonal harmony of pace at the 95 percent level of confidence given a normative sample mean of 1.5 seconds with a standard deviation of 0.33 seconds pause duration.

The present disclosure includes that contained in the appended claims, as well as that of the foregoing description. Although this invention has been described in its preferred form with a certain degree of particularly, it is understood that the present disclosure of the preferred form has been made only by way of example and that numerous changes in the details of the circuit and the combination and arrangement of circuit elements may be resorted to without departing from the spirit and the scope of the invention as hereinafter claimed.

What is claimed is:

1. A human response system for determining the rate of hiatuses between neuromotor responses of a human subject, comprising in combination:
   transducer means responsive to at least one type of monitored neuromotor response of the subject who is subjected to sensory inputs to the right and left hemispheres of the brain;
   hiatus means connected to said transducer means to determine successive occurrences of a hiatus between predetermined neuromotor responses of said at least one type of the subject, with each hiatus defined as the absence of said at least one type of monitored neuromotor responses for a predetermined time interval bounded by the predetermined neuromotor responses;
   rate means connected to said hiatus means to determine the average hiatus rate in a given segment of the predetermined neuromotor response of the subject;
   sorting means to sort the average hiatus rate into one of at least two levels of response;
   and means to indicate the average time duration of the individual hiatuses for each of the at least two rate levels.

2. A human response system as set forth in claim 1, wherein said transducer means includes a pressure transducer connected to a manual writing instrument movable by the human subject;
   said neuromotor response being a writing response with the writing instrument;
   said hiatus means determining the occurrence of hiatuses in the writing with the writing instrument; and
   said sorting means sorting the average hiatus rate into levels of response less than and greater than 100 milliseconds.

3. A human response system as set forth in claim 2, wherein said rate means includes a pressure transducer in said rate means to determine the start and finish of said given segment of the writing response of the subject.

4. A human response system as set forth in claim 2, wherein said transducer means includes an accelerometer connected to establish that signals from said pressure transducer are valid.

5. A human response system as set forth in claim 1, wherein said transducer means includes voice print processing and identifying means.

6. A human response system as set forth in claim 1, including second transducer means operable to receive second type signals from signal generators, and wherein said first-mentioned transducer means is operable to receive first type signals resulting from the response of the brain of the subject to said second type signals.

7. A human response system as set forth in claim 1, said indicating means including means indicating the average hiatus time duration for each of two persons intercommunicating, wherein two persons are disposed face-to-face, and said transducer means includes a separate microphone for each person, with the microphones disposed closely adjacent and back-to-back.

8. A human response system as set forth in claim 1, wherein said transducer means is connected to be responsive to the voice of a subject and to the voice of another in a dialogue setting;

said hiatus means connected to determine the occurrence of each of successive hesitation pauses in the speech of a subject, each of which hesitation pauses is defined as a joint silence of one second or more bounded by the speech of such subject during a dialogue;

said rate means determining the frequency of hesitation pauses in the speech of the subject during a dialogue with said another person;

said indicator means having signal codes of satisfactory, caution, and unsatisfactory associated with a numerical indication of the time duration of the pause; and a microprocessor connected to the output of said rate and sorting means and having an output to said indicator means to emphasize only one signal code of satisfactory, caution or unsatisfactory, depending on the number of pauses per minute being 0 to about 1.5, about 1.5 to 2, and more than 2, respectively, and to indicate the average time duration of those hesitation pauses which fall within the pause per minute range of 0 to about 1.5, about 1.5 to 2, and more than 2, respectively.

9. The method of determining hiatus frequency and duration of a human neuromotor response, comprising in combination:

determining the duration and occurrence of each of a plurality of hiatuses in the neuromotor response of a human subject, each hiatus defined as a lapse in the continuity of the response;

measuring the average hiatus rate in a given time segment of a response;

sorting the hiatuses into at least two rate levels; and indicating to human sensors for conscious awareness the hiatus rate level which was dominant relative to the others of the at least two rate levels and the average hiatus time duration of such level.

10. The method as set forth in claim 9, wherein the neuromotor response is an oral response, and said determining step is determining hiatuses within a spoken word monitored on a time base of the entire word.

11. The method as set forth in claim 9, for determining a neuromotor response for each of two persons communicating with each other; including approximating in real time and thus shifting from peripheral to central awareness the inner experience of one person to the other person.

12. The method as set forth in claim 9, wherein said determining step includes determining hiatuses in a segment of manual writing by the human subject, with each writing hiatus being a hiatus in the movement of the writing instrument for a period of time greater than about 100 milliseconds.

13. The method as set forth in claim 9, said determining step including:

determining the length of each of one or more hiatuses in the speech of the subject while having a dialogue bounded by speech of the subject and establishing each of such hiatuses as a hesitation pause when the length thereof exceeds about one second of time;

assigning a satisfactory code to those hesitation pauses in the speech of said subject which occur after more than about one minute of speech without a hesitation pause;

assigning a caution code to the second hesitation pause which occurs during any one minute of the dialogue;

activating a caution indicator indicating an average of about one to two hesitation pauses per minute; and said indicating step including displaying the average time duration of the dominant one of the satisfactory and caution code pauses for said subject.

* * * * *

UNITED STATES PATENT AND TRADEMARK OFFICE
CERTIFICATE OF CORRECTION

PATENT NO. : 4,802,484

DATED : February 7, 1989

INVENTOR(S) : Ernest H. Friedman, et al.

It is certified that error appears in the above-identified patent and that said Letters Patent is hereby corrected as shown below:

Column 1, line 58 "word" should be --world--.

Column 3, line 62 "occurrence" should be --occurrences--.

Column 6, line 57 "the" should be --and--.

Column 6, "," should be omitted, in line 60.

Column 7, line 20 after "stages" insert --66 and 67--.

Column 7, line 48 "a" should be omitted.

Column 12, line 8 "farily" should be --fairly--.

Column 16, in the table, under "Component" heading, line 2 "op amp 52,53" should be --op amp 52, 53,66,67--.

Column 20, line 13 "particularly" should be --particularity--.

Signed and Sealed this

Twenty-fourth Day of October, 1989

Attest:

DONALD J. QUIGG

Attesting Officer

Commissioner of Patents and Trademarks